United States Patent [19]

Michel et al.

[11] 4,124,699
[45] Nov. 7, 1978

[54] ALUMINA-BASED BODIES WITH LARGE PORES, PRODUCED BY AGGLOMERATION

[75] Inventors: Max Michel, Yerres; Jean-Paul Fort, Antony, both of France

[73] Assignee: Rhone Progil, Courbevoie, France

[21] Appl. No.: 887,543

[22] Filed: Mar. 17, 1978

Related U.S. Application Data

[63] Continuation of Ser. No. 708,229, Jul. 23, 1976, abandoned, which is a continuation of Ser. No. 451,237, Mar. 14, 1974, abandoned.

[30] Foreign Application Priority Data

Mar. 14, 1973 [FR] France ............................... 73.09088

[51] Int. Cl.$^2$ ............................................... C01F 7/02
[52] U.S. Cl. .................................... 423/628; 252/465; 252/463; 423/625
[58] Field of Search ............................... 423/625, 628

[56] References Cited

U.S. PATENT DOCUMENTS

| | | | |
|---|---|---|---|
| 3,310,366 | 3/1967 | Koepernik | 423/628 |
| 3,379,499 | 4/1968 | Moehl | 423/628 |
| 3,411,878 | 11/1968 | Grauber et al. | 423/628 |
| 3,472,787 | 10/1969 | Kiscuka | 423/628 |
| 3,520,654 | 7/1970 | Carr et al. | 423/628 |
| 3,743,709 | 7/1973 | Shaw et al. | 423/628 |
| 3,846,540 | 11/1974 | Leach | 423/628 |
| 3,958,341 | 5/1976 | Podschus | 423/628 |

FOREIGN PATENT DOCUMENTS 888,772  2/1962  United Kingdom ..................... 423/628

Primary Examiner—Herbert T. Carter
Attorney, Agent, or Firm—McDougall, Hersh & Scott

[57] ABSTRACT

The invention is addressed to very light alumina-based agglomerated bodies, the porosity of which comprises pores of large dimensions. These bodies are produced from alumina gels which are dehydrated in hot gas streams so that the amount of water remaining, which can be measured by calcination at high temperature, is from 8 to 35% of the weight of the treated gels; the treated gels to which other components can be added are agglomerated by any known means. These bodies can be used in particular in adsorption, catalysis, and chromatography.

5 Claims, No Drawings

ALUMINA-BASED BODIES WITH LARGE PORES, PRODUCED BY AGGLOMERATION

This is continuation of application Ser. No. 708,229, filed July 23, 1976, and now abandoned. Ser. No. 708,229 is a continuation is a continuation of Ser. No. 451,237, filed Mar. 14, 1974 and now abandoned.

This invention relates to very light alumina-based agglomerated bodies having pores of large dimensions.

It is known that active aluminas have textural and structural properties which are related to the various methods of their production, and can thus be put to very widely varying uses, for example in adsorption, chromatography and catalysis.

However, in most of the bodies which comprise active alumina, the porosity characteristics are related, in particular, to the specific surface area, so that bodies which have a large specific surface area have a relatively substantial porosity, but comprising pores of very small dimensions.

It is often necessary to be able to produce active alumina bodies in which fine-pore porosity has superimposed thereon porosity comprising pores of substantially larger dimensions, in order to facilitate exchanges between the interior of such bodies and the media in which they are immersed. This obviously results in a much greater total pore volume, which means that these characteristics are difficult to achieve without a substantial reduction in mechanical strength, although strength is a property which it is essential to safeguard the bodies in almost all the uses which can be envisaged.

A method which is well known, among the various methods of producing active alumina bodies, is that which comprises treating hydrated aluminas, in a stream of hot gases, the temperature of which can reach approximately 1000° C., so greatly to reduce their water content. This corresponds to producing substances whose crystalline structure is highly disorganized, processing them, if necessary, as by crushing, to a suitable grain size, moistening them, agglomerating them by any known means, maturing of the agglomerated bodies thus produced, which causes them to harden by a setting phenomenon similar to that of hydraulic binding agents, and finally activating the resulting bodies, at temperatures which depend on the specific surface area to be imparted to such bodies. This method is described in particular in French Pat. No. 1,077,163. The hydrated alumina, which is most widely used in this process, is aluminum α-trihydroxide or hydrargillite produced by the known Bayer method which provides alumina to the aluminum industry.

However, it is difficult to impart porosity comprising pores of large dimensions, to the agglomerated bodies which are produced from hydrargillite. Some methods however make it possible to achieve this aim, in particular by regulating the amount of moistening water and using a very restricted range of grain sizes; these methods are not without disadvantages, for example the industrial production of a restricted range of grain sizes is always a difficult problem as is well known.

It has now been found that this method of dehydration by hot gas streams, when applied to alumina gels, makes it possible to produce agglomerated highly porous, aluminous bodies, with pores of large dimensions, but which are nonetheless very strong.

Generally, it is known that hydrated alumina gels can be produced in various ways and from various compounds. Industrially, the methods which are most generally used comprise precipitating alumina from alkaline aluminates, in practice sodium aluminate, by acids, or precipitating alumina from various aluminum salts, by basic compounds. The pH range which permits precipitation of the alumina extends approximately from 7.5 to 11. Depending mainly on the selected pH conditions and temperature, it is possible to produce gels of varying compositions in which there is always an amorphous phase, which occurs entirely when precipitation is carried out at temperatures which are close to ambient temperature and at pH values which extend approximately from 8 to 9. Moreover, it is clear that continuous precipitation methods, which permit conditions to be kept substantially constant, are the most highly recommended for producing a substantially pure amorphous phase.

It is also known that these gels evolve with time in the presence of a large excess of aqueous phase, such evolution being governed by the amount and the nature of the anions and cations present, temperature, and the presence of various seed crystals.

As regards amorphous gels, these can be produced in the dry state only by very rapid drying, which involve, as little as possible, any substantial increase in their temperature, as long as there is a large excess of liquid water relative to combined water. In contrast, in current practice of drying in a drying oven at temperatures which are slightly above 100° C., these gels evolve in a few hours towards boehmitic forms, which are increasingly better characterized with X-rays.

However, although hydrargillite, by rapid dehydration in a stream of hot gases, is converted into disoriented complex substance comprising transition aluminas and a phase which is amorphous in respect of X-rays, which re-agglomerate by re-hydration, gels subjected to the same process, which then do not have the time to evolve towards crystalline phases, yield substances which, from the crystallographic point of view, are slightly oriented and which can also be agglomerated by the adsorption of water, preferably with an acid being added to the water used. The agglomerated bodies, which are produced in this way, after drying and activation by calcination, have porosity comprising pores of large dimensions inversely related to the amount of crystalline phases present in the initially treated gels. In practice, the temperature of the gases, depending on the degree of dehydration desired and the nature of the substances to be treated, is preferably from 350° to 1000° C., the residence times being of the order of a second.

Such treatment, which is most easily carried out on small particles resulting from atomization of aqueous suspensions of gels, can be continued until the amount of water which is contained in the resulting powdery substances and which can be measured by calcination at high temperature, is not more than about 8% by weight, nonetheless without such substances ceasing to have the property of giving solid agglomerated bodies after damping.

It should be noted that this method is very different from that described in the Pechiney-Saint Gobain French Pat. No. 1,438,497, in which totally amorphous alumina gels are dried at low temperature so that they still contain approximately 35% by weight water, which substantially corresponds to their constitution or combined water. Gels dried in this manner can be agglomerated after moistening, preferably by an ammoniacal solution, and the presence in gels submitted to this drying operation, of well defined crystalline phases of alumina is not to be recommended because, since they cannot be disorganized or disoriented at the low drying temperatures used, they do not participate in the adsorption of water and in the strength of the resulting agglomerates.

In contrast, in the present method, all the crystalline phases which may be present are disorganized and participate in the strength of the agglomerates produced, the proportion of amorphous phase acting alone on the value of the porosity comprising pores of large dimensions.

The gels, which are treated in this way, are in the form of highly porous spherical particles whose porosity, it is believed, is largely retained in the agglomerated bodies which are subsequently produced, which would be the reason for the high degree of porosity of the agglomerated bodies.

It should be noted that the amount of water, as measured by calcination at high temperature in the treated gels, can be above 8% and can reach substantially that amount measured on gels which are simply dried, that is to say, approximately 35% by weight. This loss by calcination can be increased as the amount of amorphous phase contained in the gels increases. In practice however, since on an industrial basis, the treated gels contain other crystalline phases, losses which are measured by calcination at from approximately 8 to 25% by weight are the most attractive and correspond to a relatively high degree of crystallographic disorganization in the crystalline phases which may be present, which disorganization can be obtained only by treating the gels with gases at relatively high temperatures.

Finally, it is obvious that, due to the agglomerating properties of the alumina gels treated in this way, it is possible to add particular bodies of any nature whatever, and in particular particles of aluminas of various crystalline varieties, which may or may not be treated in hot gas streams, as well as particles of zeolites or molecular sieves. In addition, these agglomerated bodies can comprise elements or compounds having catalytic effects of different natures, and in particular oxides and metals which are added, or whose precursors have been added, before the gaseous heat treatment, after such treatment, or after the formation of the agglomerated bodies, or even to sodium aluminate in order to produce precipitation of the alumina. Finally, it is possible also to modify the pore characteristics of the agglomerated bodies in accordance with the previously known methods which comprise, for example, carrying out hydrothermal treatments, controlling the amounts of agglomerating water, the range of grain sizes, and adding particles of various shapes which can disappear after agglomeration, by decomposition, vaporization, dissolution, combustion, calcination or any other means. Clearly the amount of these various additives must be such that the strength of the substances produced is not excessively reduced.

Various examples are given hereinafter in order to illustrate the present invention. These examples, concerning agglomerates in the form of balls which are produced in a rotary granulator, the last two examples being comparative examples; one concerns balls produced from a gel which is dried by atomization at a low temperature and the other relates to balls which are produced from a gel which is calcined in an oven until it contains an amount of water, which can be measured by calcination at higher temperature, comprised within the preferred range mentioned above. These two examples are given in order clearly to show the specific nature of the rapid action of hot gases on the nature of the results obtained. The results in all of the examples, concerning balls which are calcined at 700° C. and then at 1000° C., are summarized in the accompanying table which also gives the pore characteristics of the balls, their specific surface area in sq. m/g, their resistance to grain-by-grain crushing in kg, which is an average over 10 balls, and their resistance to attrition, which is expressed in percent by weight of the balls which remains after wear by agitation for five minutes in a microcrusher.

These examples are not given by way of limitation of the invention in that other general methods of agglomerating particulate substances can be used with similar results, such as agglomeration by compression and agglomeration by extrusion.

EXAMPLE 1

A solution of sodium aluminate, having 100 g/l of alumina expressed as $Al_2O_3$, is precipitated continuously at a pH value maintained at 8.7 and at a temperature of 35° C., by addition of a N nitric acid solution.

The alumina gel suspension, which issues from the reaction vessel, then passes, for purposes of homogenization, into a buffer tank which is maintained at a temperature of 35° C., for which it is passed over a continuous filter. The resulting cake which comprises aluminum hydroxide, which is virtually amorphous in respect of X-rays, is washed with permuted water until the ions in the filtrate disappear, and then drained. The drained cake is then resuspended by stirring in the permuted water so that it can be sprayed as by means of a nozzle at the base of an apparatus, for dehydration by a rising stream of hot gases produced by the burning of propane. The inlet temperature of the gases is 550° C., their outlet temperature is 300° C., and the contact time is about one second. The resulting powder, which is separated from the gases in a cyclone separator, has a water loss measured by calcination at high temperature of 24%, and an apparent density of 0.30g/ccm. It is formed of substantially spherical particles having a diameter of less than 100 microns, with 70% of such particles having a diameter of less than 44 microns. This powder is moistened by means of an aqueous N/2 nitric acid solution and agglomerated in the form of balls in a rotary granulator. The balls are then kept in a closed vat for a period of 8 hours at a temperature of 30° C., dried in a gas flow at 200° C. and then calcined for two hours at 700° C. The balls are then screened so as to retain only those whose diameters are from 2.4 to 4 mm. A fraction of the graded balls is then calcined for 24 hours at 1000° C.

EXAMPLE 2

An alumina gel cake is prepared in a similar manner to the mode of operation described in Example 1, except that the pH-value in this case is fixed at around 8.0 and temperature is fixed at about 30° C. The suspension, issuing from the precipitation reaction vessel, passes into the buffer tank at 30° C., before being passed over the filter. The cake, which is also substantially amorphous, is washed, re-suspended, treated in the hot gas flow and converted into balls, in the manner described in Example 1. The balls produced in this manner are dried, graded and calcined in the same manner.

EXAMPLE 3

Balls are prepared in a rotary granulator as set out in Example 1, but after agglomeration and before drying, the balls are subjected to a hydro-thermal treatment for 5 hours at 100° C. in a saturating vapor. The balls are then treated as in Example 1. The vapor treatment of the crude balls makes it possible to increase the strength of the balls, by reducing their pore volume.

EXAMPLE 4

A mixture is made which contains by weight 50% of the same powder as that produced in Example 1, and 50% of a 5 A molecular sieve of mono-crystals of from 2 to 5 microns. This mixture is agglomerated in a rotary granulator after moistening with a N/2 nitric acid solution. The balls produced are subjected to a hydro-thermal treatment for 5 hours at 100° C. in a closed vessel. Calcination at 700° C. for a period of 2 hours is then effected.

EXAMPLE 5

A powder having the formula $2CuO.1\ Cr_2O_3$ is prepared by calcination at 400° C. of an intimate mixture of cupric nitrate and chromic anhydride. This powder is mixed with the alumina powder produced as set out in Example 1, in a proportion of 18% by weight of oxides with respect to the alumina. Agglomeration is effected, followed by maturing and calcination under the same conditions as in Example 1. By virtue of its macroporosity, this catalyst has a high degree of activity as regards the oxidation of carbon monoxide and the hydrocarbons present in very substantial gas flows. It also has a degree of stability which is higher than that of catalysts containing the same oxides deposited by impregnation.

EXAMPLE 6

This example is given by way of comparison and relates to a gel which is dried at moderate temperature. An alumina cake is prepared as set out in Example 1. This cake is re-suspended and then dried in an atomizer in which the inlet temperature of the gases is 180° C. and the outlet temperature is 80° C. The powder which is collected, which is virtually amorphous, has a water loss, as measured by calcination at high temperature, of 40% by weight, and an apparent density of 0.85 g/ccm, which is much higher than that of the powder of Example 1. This powder is converted into balls in a rotary granulator and the balls are then treated in the same manner as in Example 1.

EXAMPLE 7

This example is also given by way of comparison and concerns a gel which is calcined in an oven. The same alumina cake as that of Example 1 is dried in a drying oven, coarsely crushed and calcined in an oven at 500° C. so that the water loss, by calcination at high temperature of this cake, is 10% by weight. It is then crushed into the form of powder having particles which are smaller than 100 microns. This powder has a density of 0.65g/ccm and is agglomerated in the form of balls in a rotary granulator as in Example 1. The balls produced are treated in an identical manner.

TABLE

| Balls calcined at 700° C | EXAMPLES | | | | | | |
|---|---|---|---|---|---|---|---|
| | 1 | 2 | 3 | 4 | 5 | 6 | 7 |
| Total pore volume ccm/g | 1.15 | 1.11 | 0.85 | 0.50 | 0.95 | 0.60 | 0.65 |
| Macroporous volume (pores of diameter 0.05 micron) ccm/g | 0.47 | 0.43 | 0.20 | 0.10 | 0.35 | 0.14 | 0.15 |
| Specific surface area sq. m/g | 250 | 230 | 220 | 410 | 190 | 250 | 300 |
| Mean resistance to crushing kg | 4.5 | 4.0 | 6.0 | 3.0 | 3.0 | 7.0 | 8 |
| Resistance to attrition % | 99.8 | 99.8 | 99.6 | 98 | 98 | 99.5 | 99 |

| Balls calcined at 700° C then 1000° C | EXAMPLES | | | | | | |
|---|---|---|---|---|---|---|---|
| | 1 | 2 | 3 | 4 | 5 | 6 | 7 |
| Total pore volume ccm/g | 1.08 | 1.00 | 0.80 | — | 0.85 | 0.58 | 0.60 |
| Specific surface area sq.m/g | 120 | 95 | 110 | — | 85 | 95 | 100 |
| Mean resistance to crushing kg | 3.0 | 3.1 | 4.0 | — | 2.3 | 6.2 | 7 |
| Resistance to attrition % | 99.7 | 99.5 | 99.7 | — | 97 | 99.3 | 99 |

This table clearly shows that, in spite of their large pore volume, all the alumina agglomerates have a good mechanical strength, particularly as regards attrition, and that even the agglomerates which are half composed of molecular sieves (Example 4) still have levels of strength which are sufficient for them to be employed in industrial uses. This table also shows, by comparison between the results of Examples 6 and 7, and the results of Examples 1, 2 and 3, that the large pore volumes are obtained solely by using gels which are dehydrated rapidly in a stream of hot gases.

We claim:

1. The method of producing high strength bodies of alumina having pores of large dimension comprising precipitating an amorphous alumina gel from an aluminate solution with acid at a pH within the range of 8 to 9, separating and washing the precipitated gel particles, re-suspending the separated gel particles in aqueous medium, dehydrating the amorphous gel particles by spraying into a stream of hot gas at a temperature within the range of 350° C. to 1000° C. rapidly to remove the water to a residual water content of 8 to 35% by weight to yield highly porous spherical particles having a diameter of less than 100 $\mu$ and in which the crystalline phases are highly disorganized; moistening the dehydrated gel particles in acidic solution and agglomerating the moistened particles, drying the formed agglomerate, and then calcining the dried agglomerate to form agglomerated bodies having pores of large dimension.

2. The method as claimed in claim 1 in which the amorphous gel particles are dehydrated by exposure to a gas stream at a temperature within the range of 350° C. to 1000° C. for about one second.

3. The method as claimed in claim 1, in which the agglomeration is effected by compression.

4. The method as claimed in claim 1, in which the agglomeration is effected by extrusion.

5. A method of producing bodies as claimed in claim 1, characterized in that agglomeration is effected in a rotary granulator.

* * * * *